United States Patent [19]

Tomiyama et al.

[11] Patent Number: 4,780,462
[45] Date of Patent: Oct. 25, 1988

[54] ANTIHYPERTENSIVE 1,5-BENZOTHIAZEPINE DERIVATIVES AND COMPOSITIONS THEREOF

[75] Inventors: Tsuyoshi Tomiyama, Nagano; Naoto Ueyama, Ueda; Yumiko Ichikawa, Nagano, all of Japan

[73] Assignee: Kotokuki Seiya Kau Co., Ltd., Nagano, Japan

[21] Appl. No.: 70,414

[22] Filed: Jul. 7, 1987

[30] Foreign Application Priority Data

Dec. 25, 1986 [JP] Japan .................................. 61-311568

[51] Int. Cl.$^4$ ...................... A61K 31/55; C07D 285/36
[52] U.S. Cl. ....................................... 514/211; 540/552
[58] Field of Search ........................ 540/552; 514/211

[56] References Cited

U.S. PATENT DOCUMENTS 4,584,292 4/1986 Tomiyama ........................ 540/552

OTHER PUBLICATIONS

Theilheimer, *Synthetic Methods of Organic Chemistry*, 1952, p. 145, p. 182.

*Primary Examiner*—Mary C. Lee
*Assistant Examiner*—Zinna Northington
*Attorney, Agent, or Firm*—Emmanuel J. Lobato; Robert E. Burns

[57] ABSTRACT

A new series of 1,5-benzothiazepine analogues are disclosed. These compounds are represented by the following general formula:

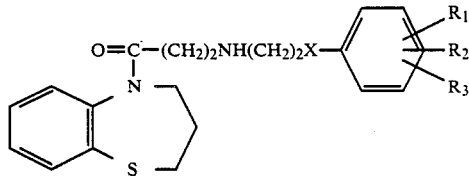

wherein $R_1$, $R_2$ and $R_3$ each represent hydrogen, a lower alkyl, nitro, amino, lower-alkyl-oxy or halogen group, X represents O or S. These compounds are useful as anti-hypertensive agents.

14 Claims, No Drawings

ANTIHYPERTENSIVE 1,5-BENZOTHIAZEPINE DERIVATIVES AND COMPOSITIONS THEREOF

BACKGROUND OF THE INVENTION

This invention relates to new 1,5-benzothiazepine derivatives, therapeutic compositions containing these derivatives and the method of manufacturing the same.

SUMMARY OF THE INVENTION

The principal object of the present invention is the provision of novel compounds having advantageous pharmaceutical properties. Another object of the present invention is the provision of pharmaceutical compositions useful as antihypertensive agents. Still another object of the present invention is the provision of new 1,5-benzothiazepine derivatives and a method for the manufacture thereof. These and other objects of the invention will become apparent from the description that follows hereinafter.

DETAILED DESCRIPTION OF THE INVENTION

This invention relates to new 1,5-benzothiazepine derivatives and their acid-addition salts, and a method of synthesis and use of them as potent antihypertensive agents.

The compounds of the this invention are represented by the general formula(I):

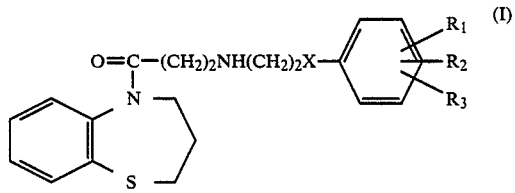

wherein;
$R_1$, $R_2$, $R_3$ each represents H, a lower alkyl, nitro, amino, loweralkyloxy or halogen atom and X represents O or S.

The term "lower alkyl" as used herein designates normal or branched $C_{1-5}$ alkyl groups. The compounds related to the general formula(I) are as follows.

(1) 5-[3-(2-(2-,6-dimethoxyphenoxy)ethylamino)-propionyl]-2,3,4,5-tetrahydro-1,5-benzothiazepine·fumarate.
(2) 5-[3-(2-(3,4,5-trimethoxyphenoxy)ethylamino)-propionyl]-2,3,4,5-tetrahydro-1,5-benzothiazepine·fumarate.
(3) 5-[3-(2-(2,6-diisopropylphenoxy)ethylamino)-propionyl]-2,3,4,5-tetrahydro-1,5-benzothiazepine·fumarate.
(4) 5-[3-(2-(2,6-dimethylphenoxy)ethylamino)propionyl]-2,3,4,5-tetrahydro-1,5-benzothiazepine·fumarate.
(5) 5-[3-(2-(4-nitrophenylthio)ethylamino)propionyl]-2,3,4,5-tetrahydro-1,5-benzothiazepine·fumarate.
(6) 5-[3-(2-(3-aminophenoxy)ethylamino)propionyl]-2,3,4,5-tetrahydro-1,5-benzothiazepine·fumarate.
(7) 5-[3-(2-(3-nitrophenoxy)ethylamino)propionyl]-2,3,4,5-tetrahydro-1,5-benzothiazepine·fumarate.
(8) 5-[3-(2-(4-methoxyphenoxy)ethylamino)propionyl]-2,3,4,5-tetrahydro-1,5-benzothiazepine·fumarate.
(9) 5-[3-(2-(2,4-dichlorophenoxy)ethylamino)propionyl]-2,3,4,5-tetrahydro-1,5-benzothiazepine·fumarate.
(10) 5-[3-(2-(4-methylphenoxy)ethylamino)propionyl]-2,3,4,5-tetrahydro-1,5-benzothiazepine·fumarate.
(11) 5-[3-(2-(3-methylphenoxy)ethylamino)propionyl]-2,3,4,5-tetrahydro-1,5-benzothiazepine·fumarate.
(12) 5-[3-(2-(2,4,6-trimethylphenoxy)ethylamino)propionyl]-2,3,4,5-tetrahydro-1,5-benzothiazepine·fumarate.
(13) 5-[3-(2-(2,4-dichlorophenoxy)ethylamino)propionyl]-2,3,4,5-tetrahydro-1,5-benzothiazepine·fumarate.
(14) 5-[3-(2-(2-nitrophenoxy)ethylamino)propionyl]-2,3,4,5-tetrahydro-1,5-benzothiazepine·fumarate.
(15) 5-[3-(2-(2-aminophenoxy)ethylamino)propionyl]-2,3,4,5-tetrahydro-1,5-benzothiazepine·fumarate.
(16) 5-[3-(2-(4-nitrophenoxy)ethylamino)propionyl]-2,3,4,5-tetrahydro-1,5-benzothiazepine·fumarate.
(17) 5-[3-(2-(2,6-dimethylphenylthio)ethylamino)propionyl]-2,3,4,5-tetrahydro-1,5-benzothiazepine·fumarate.
(18) 5-[3-(2-(3-methylphenylthio)ethylamino)propionyl]-2,3,4,5-tetrahydro-1,5-benzothiazepine·fumarate.

The above-mentioned compounds numbered from 1 to 18, will be refferred to hereinafter, as Compound 1, Compound 2–Compound 18, respectively.

The compounds of the general formula(I) can be prepared by reacting 2,3,4,5-tetrahydro-1,5-benzothiazepine of the formula(II) with a compound of the formula(III):

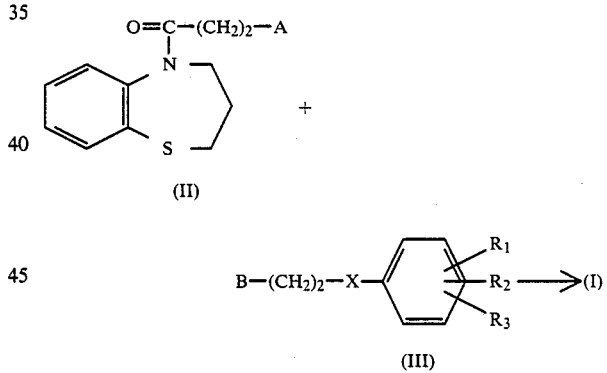

wherein;
A is an amino or halogen group;
B is halogen, p-toluensulfonyl or amino and other symbols are same as defined before.

In case A is an amino group in the formula(II), a compound of the formula (IIIa) in which B is halogen atom or a p-toluenesulfonyl group, is reacted with a compound of the formula (IIa) to give a compound of the general formula(I):

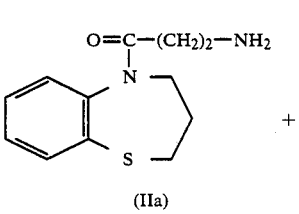

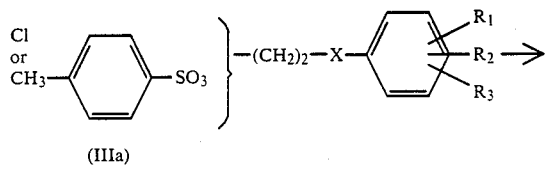

(IIIa)

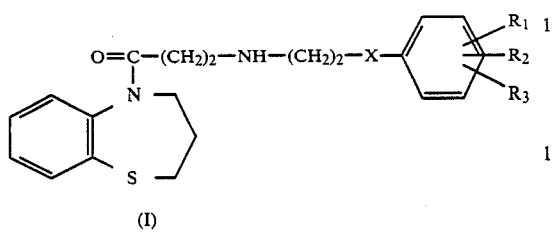

(I)

wherein $R_1$, $R_2$, $R_3$ and X are the same as mentioned above.

Alternatively when A is halogen in the formula(II), a compound of the formula (IIIb) in which B is an amino group, is reacted with a compound of the formula (II) as follows.

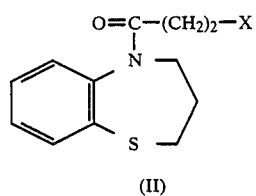

(II)

+

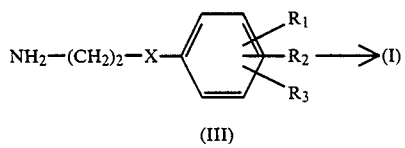

(III)

wherein $R_1$, $R_2$, $R_3$ and X are the same as mentioned above.

The reaction of compound of the formula(II) and with a compound of the formula (III) can be carried out in an inert solvent like benzene or toluene. Sodium hydroxide, potassium carbonate and sodium ethylate, besides organic bases such as triethylamine, isopropylamine or pyridine may be employed. Excess amine (cf. biequivalent) of compound(IIa) or compound(IIIb) can also be employed.

The compound of the formula(II) can be obtained by reacting 2,3,4,5-tetrahydrobenzothiazepine, prepared according to the method of H. J. Federsel (Tetrahedron Letter, 21, 2429p, 1980), with a compound of formula(IV):

ClCO(CH$_2$)$_2$A    (IV)

wherein A is the same as mentioned above. The compound(III) can be prepared as follows.

In case B is a halogen atom:

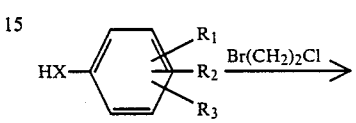

In case B is a p-toluensulfonyl group:

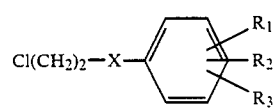

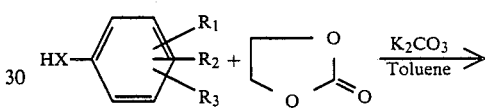

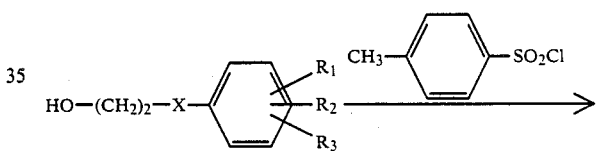

In case B is an amino group:

A halogen or p-toluenesulfonyl compound of the formula(IIIa) is reacted with potassium phthalimide and decomposed with hydrazine so that a compound of the formula(IIIb) can be obtained.

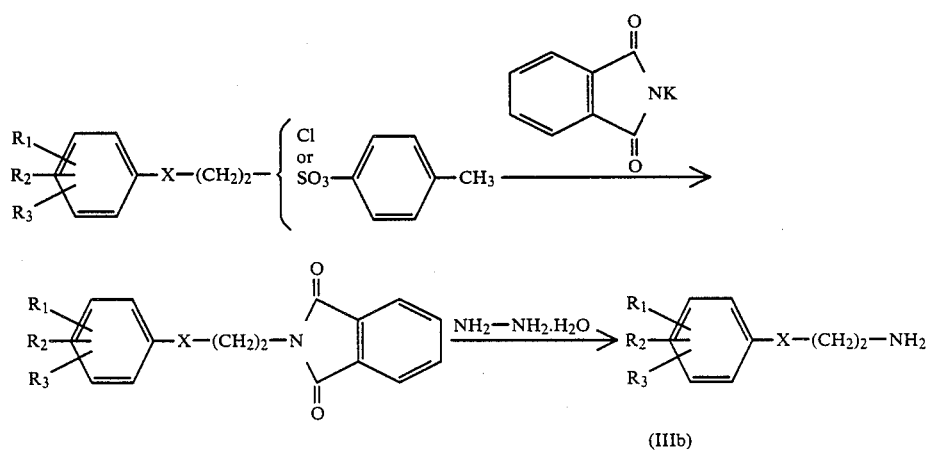

(IIIb)

The compound(I) thus obtained can be applied as a free base or acid-addition salt such as hydrochloride, lactate and fumarate.

The compounds of the invention have a vasodilating effect and are useful as antihypertensive agents. The compounds of the invention can be administered both perorally and parenterally in the form of tablets, capsules, granules, syrups, suppositories and injections. Doses to be administered are various depending on the patients condition and age. One effective dosage of the compound of this invention is 100 mg-150 mg for adults, three times a day. The following example illustrates pharmacological data and procedures for preparing the active compounds of the invention.

Pharmacological Experiment 1

$Ca^{++}$-Antagonistic activity. Experiments are carried out according to the method of M. Ferrari (Arch. Intern. Pharmacoadyn. 174, 223 (1968) Guinea-pig *taenia caecum* is isolated and suspended in a bath which is filled with $Ca^{++}$-free Krebs Ringer solution for 30 minutes. In this condition, *taenia caecum* is contracted by elevating $Ca^{++}$-ion concentration of Krebs Ringer and obtained a dose-response curve against $Ca^{++}$-ion. Pretreatment with the compound of this invention before 3 minutes, and obtained a dose-response curve under the existence of the compound of this invention.

From these two dose-response curves, $PA_2$ value is calculated and $PA_2$ is expressed as index of activities. (Table 1)

TABLE 1

| Compound No. | PA₂ value |
|---|---|
| 1 | 6.09 |
| 4 | 6.99 |
| 5 | 7.01 |
| 7 | 6.61 |
| 8 | 6.22 |
| 12 | 7.26 |
| 13 | 6.90 |

Pharmacological Experiment 2

The coronary artery dilating activity of the compounds is estimated by Rangendorf method (Pfugers. Arch. Ges. Physiol. 62, 291 (1895)) using the isolated guinea-pig heart. The maximum of increased coronary blood flow is examined for 2 minutes and results of test compounds are summarized in Table 2.

TABLE 2

| Compound No. | Concentraton (μg/heart) | maximum increased blood flow (ml) |
|---|---|---|
| 4 | 10 | 7.2 |
|  | 30 | 19.2 |
| 6 | 10 | 4.6 |
|  | 30 | 6.0 |
| 11 | 3 | 7.7 |
|  | 30 | 16.5 |
| 12 | 10 | 11.3 |
|  | 30 | 18.3 |
| 15 | 30 | 2.0 |
| 16 | 10 | 4.2 |

Pharmacological Experiment 3

The antihypertensive activities of the compounds on anesthetized normotensive rats were tested according to the method of H. Sogabe.[1] Male Wistar rats weighing 200-300 g were anesthetized with urethane (1.2 g/kg. i.v.). Blood pressure was measured by a transducer (Nihon Koden RT-5) connected the catheter inserted into the femoral artery. The test compounds in physiological saline (0.1 ml/100 g. B.W.) were injected via the femoral vein. The antihypertensive activity was assessed by comparing with $MBP_{15}$ (dose which lowers the mean blood pressure by 15 mmHg, mg/kg i.v.). The results are shown in Table 3.

(1) Hirobumi Sogabe "Jikken Kouketsuatsushou nyuumon" p227 (Eikoudo 1968).

TABLE 3

| Compound No. | Antihypertensive act. (M.B.P.₁₅) |
|---|---|
| 3 | 1.35 (μg) |
| 5 | 2.0 |
| 7 | 4.2 |
| 9 | 80.6 |
| 11 | 34.7 |
| 13 | 3.5 |
| 17 | 9.3 |

Acute Toxicity

The acute toxicity of the compounds of this invention in mice per os is as follows. (Table 4)

TABLE 4

| Compound No. | LD₅₀ (mg/kg) |
|---|---|
| 3 | 1498 |
| 15 | 374 |

[Reference Example]

2-(2,6-Dimethoxyphenoxy)ethylamine (1) 2,6-Dimethoxyphenoxyethanol

A mixture of 6.0 g of 2,6-dimethoxyphenol, 6.8 g of ethylene carbonate and 5.4 g of potassium carbonate in 40 ml of toluene was refluxed for 17 hours. After cooling, toluene solution was separated, dried ($Na_2SO_4$) and solvent was evaporated. 7.77 g of desired compound was obtained.

M.S.(m/e) 198(M+), 139(B.P.)

(2) 2,6-Dimethyoxyphenoxyethylchloride

A solution of 7.77 g of 2,6-dimethoxyphenoxyethanol in 30 ml of pyridine was cooled and 4.7 g of thionylchloride was added with stirring. After 20 minutes, stirring, the reaction mixture was heated on the steam bath for 2 hours. After cooling, the reaction mixture was evaporated in reduced pressure. The residue was extracted with $CHCl_3$, purified with silicagel chromatography (eluent: EtOAc) 1.82 g of objective compound was obtained.

M.S.(m/e). 217(M++1), 153(B.P.)

(3) 2-(2,6-Dimethoxyphenoxy)ethylasmine

A mixture of 1.82 g of compound obtained from (2) and 1.7 g of phthalimide in 25 ml of Dimethylformamide was heated (100° C.) for 9 hours. After cooling, resulted precipitate was filtered and precipicate was washed with dimethylformamide. Filtrate and washing was combined and the solvent was evaporated in reduced pressure. The residue was dissolved in chloroform and washed with brine, dried ($Na_2SO_4$) and the solvent was evaporated. Ether was added to the residue, 1.6 g of white crystal was obtained. Obtained 1-(2,6-dimethoxyphenoxyethyl)phthalimide (1.6 g) was dissolved in ethanol (30 ml) and hydrazine hydrate (0.49 g) was added. After refluxing for 1 hour, the reaction mixture was cooled and filtered to remove the insoluble material. The filtrate was evaporated and the residue was extracted with 5% HCl solution. 5% HCl extract was basified with potassium carbonate and extracted with chloroform. Chloroform extract was dried (Na$_2$SO$_4$) and evaporated. 1.0 g of objective compound was obtained.

M.S.(m/e) 196(M$^+$ −1), 154(B.P.)

The compound obtained from above mentioned procedure (1) was reacted with fumaric acid and objective compound was obtained. m.p. 115°–117° C.

I.R.(cm$^{-1}$) 3450, 2950, 1710, 1650, 1610, 1500, 1480, 1450, 1420, 1300, 1260, 1170.

The following compound of Table 5 were obtained as same manner as the Example 1.

TABLE 5

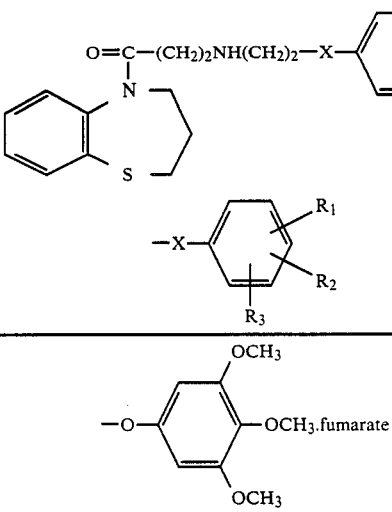

| Compd. No. | | Physical Properties |
|---|---|---|
| 2 | 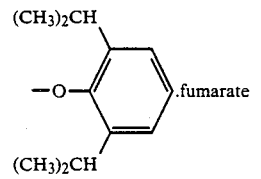 | m.p. 151~153° C.<br>M.S.(m/e)446(M$^+$-fumaric acid) |
| 3 | 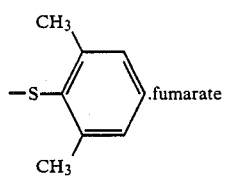 | m.p. 176~178° C.<br>M.S.(m/e)440(M$^+$-fumaric acid) |
| 17 | 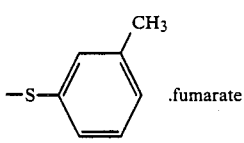 | m.p. 149~150° C.<br>M.S.(m/e)400(M$^+$-fumaric acid) |
| 18 |  | m.p. 139~140° C.<br>M.S.(m/e)386(M$^+$-fumaric acid) |

[Example 1]

5-[3-(2-(2,6-Dimethoxyphenoxy)ethylamino)-propionyl]-2,3,4,5-tetrahydro-1,5-benzothiazepine·fumarate (Compound 1)

(1) 5-[3-(2,6-Dimethoxyphenoxy)ethylamino)-propionyl]-2,3,4,5-tetrahydro-1,5-benzothiazepine A mixture of 2-(2,6-Dimethoxyphenoxy)ethylamine (0.44 g) and (5-(3-Chloropropionyl)-2,3,4,5-tetrahydro-1,5-benzothiazepine (0.282 g) in toluene (20 ml) was refluxed for 20 hours. After cooling, precipitate was removed by filtration and filtrate was concentrated. The residue was purified with silica gel chromatograpy (eluent CHCl$_3$:MeOH=10:1). 0.03 g of objective compound was obtained.

I.R.(cm$^{-1}$) 3430, 2950, 2850, 1650, 1610, 1500, 1490, 1450, 1420, 1300, 1260

(2) Fumarate

[Example 2]

5-[3-(2-(2,6-Dimethylphenoxy)ethylamino)-propionyl-2,3,4,5-tetrahydro-1,5-benzothiazepine·fumarate (Compound 4)

(1) 2,6-Dimethylphenoxyethyltosylate

A solution of 2,6-dimethylphenoxyethanol (0.5 g) in pyridine (1.0 ml) was cooled with water and p-toluene sulfonylchloride (0.63 g) was added. After stirring for 1.5 hours, the solvent was evaporated and the residue was dissolved in chloroform. The chloroform solution was washed with water and brine, and dried (Na$_2$SO$_4$), and the solvent was evaporated. The residue was purified with silica gel chromatography (eluent: CHCl$_3$): Oily objective compound (0.50 g) was obtained.

I.R.(cm$^{-1}$) 2940, 1600, 1480, 1400, 1370, 1270, 1210, 1180, 1100, 1080, 1030, 930, 830, 780.

M.S.(m/e) 320(M+), 199(B.P.)

(2)

5-[3-(2-(2,6-Dimethylphenoxy)ethylamino)-propionyl-2,3,4,5-tetrahydro-1,5-benzothiazepine·fumarate (Compound 4)

0.5 g of the compound obtained from above mentioned procedure (1) and 0.405 g of 5-(3-Aminopropionyl)-2,3,4,5-tetrahydro-1,5-benzothiazepine was dissolved in 20 ml of toluene, and added 0.07 g of sodium hydroxide. The reaction mixture was refluxed for 7.5 hours. After cooling, the reaction mixture was washed with water and brine, and dried ($Na_2SO_4$), and evaporated. The residue was purified with silica gel chromatography (eluent: $CHCl_3$). Oily compound (0.273 g) was reacted with fumaric acid and white crystal objective compound (0.244 g) was obtained. m.p. 238°–241° C.

I.R.($cm^{-1}$) 3450, 2950, 1705, 1650, 1580, 1470, 1440, 1280, 1260, 1200, 1160, 770, 640

M.S.(m/e) 383(M+ −1-fumaric acid) 249(B.P.)

The following compounds of Table 6 were obtained as same manner as the Example 2.

TABLE 6

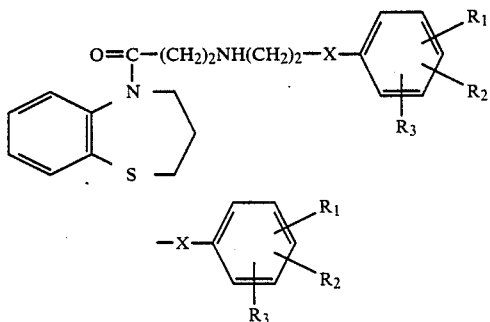

| Compd. No. | | m.p. (°C.) |
|---|---|---|
| 5 | —S—⟨C6H4⟩—$NO_2$·fumarate | 154–155° C. |
| 6 | —O—⟨C6H4⟩—$NH_2$·fumarate | 150~152° C. |
| 7 | —O—⟨C6H4⟩—$NO_2$·fumarate | 139–141° C. |
| 8 | —O—⟨C6H4⟩—$OCH_3$·fumarate | 159~161° C. |
| 9 | —O—⟨C6H3⟩(Cl)(Cl)·fumarate | 159–161° C. |
| 10 | —O—⟨C6H4⟩—$CH_3$·fumarate | 158~159° C. |
| 11 | —O—⟨C6H4⟩—$CH_3$·fumarate | 143~145° C. |

TABLE 6-continued

Structure:
O=C—(CH₂)₂NH(CH₂)₂—X—Ar(R₁,R₂,R₃), attached to N of 2,3,4,5-tetrahydro-1,5-benzothiazepine

| Compd. No. | —X—Ar(R₁,R₂,R₃) | m.p. (°C.) |
|---|---|---|
| 12 | —O—(3,5-dimethyl-4-CH₃-phenyl).fumarate | 181~183° C. |
| 13 | —O—(2-Cl,4-Cl-phenyl).fumarate | 162~164° C. |

[Example 3]

5-[3-(2-(2-Nitrophenoxy)ethylamino)propionyl]-2,3,4,5-tetrahydro-1,5-benzothiazepine·fumarate (Compound 14)

A mixture of 2-Nitrophenoxyethylchloride (0.26 g), 5-(3-Amino-propionyl)-1,5-benzothiazepine (0.355 g) and potassium carbonate (0.210 g) in toluene (15 ml) was refluxed for 16 hours. After cooling, objective compound (0.184 g) was obtained according to the method of experimental 1. m.p. 178°–180° C.

I.R.(cm⁻¹) 3450, 3000, 2800, 1690, 1650, 1610, 1580, 1510, 1470, 1430, 1410, 1360, 1280, 1250, 1160, 1020, 970, 780, 750.

M.S.(m/e) 402(M⁺ + 1-fumaric acid), 56(B.P.)

The following compound in Table 7 were obtained as same manner as the Example 3.

TABLE 7

| Compd. No. | —X—Ar(R₁,R₂,R₃) | Physical Properties |
|---|---|---|
| 15 | —O—(3-NH₂-phenyl).fumarate | m.p. 158~160° C. M.S.(m/e)372(M⁺-fumaric acid) 263(B.P.) |
| 16 | —O—(4-NO₂-phenyl).fumarate | m.p. 154~156° C. M.S.(m/e)402(M⁺-fumaric acid) 249(B.P.) |

[Example 4] (Tablet)

| | |
|---|---|
| Compound 3, | 50 parts |
| Lactose, | 30 parts |
| Crystalline cellulose, | 56 parts |

-continued

| Calcium stearate, | 4 parts |

Preparation

The ingredients are intimately admixed with each other, and the resulting mixture is compressed into 150 mg-tablets in a conventional manner.

[Example 5] (Capsules)

Capsule fillers having the same compositions as example 22 are filled into gelatin capsules of a suitable size in a conventional manner.

[Example 6] (Granules)

| Compound 15, | 50 parts |
| Lactose, | 80 parts |
| Cornstarch, | 26 parts |
| Methly cellulose, | 4 parts |

Preparation

The admixed ingredients of compound 16, lactose and cornstarch are granulated using a methly cellulose solution and dried to make granules.

What we claim is:

1. A compound of the formula:

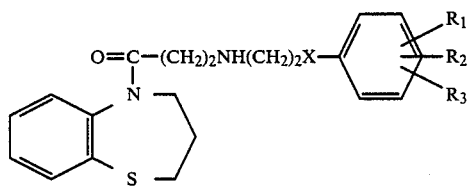

wherein:

$R_1$, $R_2$ and $R_3$ each represent hydrogen, a lower alkyl, nitro, amino, loweralkyloxy or halogen group, X represents O or S.

2. A compound according to claim 1, wherein X is O.
3. A compound according to claim 1, wherein X is S.
4. A compound according to claim 2, wherein $R_1$, $R_2$ and $R_3$ each are loweralkyl groups, or hydrogen atom.
5. A compound according to claim 2, wherein $R_1$, $R_2$ and $R_3$ each are loweralkoxy groups.
6. A compound according to claim 2, wherein $R_1$, $R_2$ and $R_3$ each are nitro or amino groups.
7. A compound according to claim 2, wherein $R_1$, $R_2$ and $R_3$ each are halogen groups.
8. A therapeutic composition for inhibiting hypertension comprising a pharmaceutically acceptable carrier and, as an active ingredient, a compound as defined in claim 1 in an amount effective to inhibit hypertension.
9. A therapeutic composition for inhibiting hypertension comprising a pharmaceutically acceptable carrier and, as an active ingredient, a compound as defined in claim 2 in an amount effective to inhibit hypertension.
10. A therapeutic composition for inhibiting hypertension comprising a pharmaceutically acceptable carrier and, as an active ingredient, a compound as defined in claim 3 in an amount effective to inhibit hypertension.
11. A therapeutic composition for inhibiting hypertension comprising a pharmaceutically acceptable carrier and, as an active ingredient, a compound as defined in claim 4 in an amount effective to inhibit hypertension.
12. A therapeutic composition for inhibiting hypertension comprising a pharmaceutically acceptable carrier and, as an active ingredient, a compound as defined in claim 5 in an amount effective to inhibit hypertension.
13. A therapeutic composition for inhibiting hypertension comprising a pharmaceutically acceptable carrier and, as an active ingredient, a compound as defined in claim 6 in an amount effective to inhibit hypertension.
14. A therapeutic composition for inhibiting hypertension comprising a pharmaceutically acceptable carrier and, as an active ingredient, a compound as defined in claim 7 in an amount effective to inhibit hypertension.

* * * * *